United States Patent
Ionescu et al.

(10) Patent No.: US 11,389,096 B2
(45) Date of Patent: Jul. 19, 2022

(54) BIO-FLUID COLLECTION AND SENSING DEVICE, SYSTEM AND METHOD

(71) Applicant: ECOLE POLYTECHNIQUE FEDERALE DE LAUSANNE (EPFL), Lausanne (CH)

(72) Inventors: Mihai Adrian Ionescu, Ecublens (CH); Hoël Guerin, Lausanne (CH); Erick García Cordero, Renens (CH); Francesco Bellando, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 27 days.

(21) Appl. No.: 15/453,920

(22) Filed: Mar. 9, 2017

(65) Prior Publication Data
US 2018/0070869 A1 Mar. 15, 2018

(30) Foreign Application Priority Data
Sep. 10, 2016 (EP) .................................... 16188227

(51) Int. Cl.
*A61B 10/00* (2006.01)
*A61B 5/00* (2006.01)
(Continued)

(52) U.S. Cl.
CPC ...... *A61B 5/1477* (2013.01); *A61B 5/150358* (2013.01); *A61B 5/4266* (2013.01);
(Continued)

(58) Field of Classification Search
CPC . A61B 5/1477; A61B 10/0045; A61B 5/4266; A61B 5/150358;
(Continued)

(56) References Cited

U.S. PATENT DOCUMENTS 4,441,373 A * 4/1984 White ................ A61B 10/0045
422/922
4,902,629 A * 2/1990 Meserol ............ B01L 3/502738
422/504
(Continued)

FOREIGN PATENT DOCUMENTS

WO WO2012050873 A2 4/2012
WO WO 2016028497 2/2016

OTHER PUBLICATIONS

Song H, Ismagilov RF. "Millisecond Kinetics on a Microfluidic Chip Using Nanoliters of Reagents.";Journal of the American Chemical Society. 2003;125 (47), 14613-14619 (Year: 2003).*
(Continued)

*Primary Examiner* — Allen Porter
*Assistant Examiner* — Samuel C Kim
(74) *Attorney, Agent, or Firm* — Andre Roland S.A.; Nikolaus Schibli

(57) ABSTRACT

An on-body wearable bio-fluid collection and sensing device including an interface or interface surface comprising at least one biocompatible material for contacting a bodily part; at least one inlet for receiving the bio-fluid, at least one outlet for evacuating the bio-fluid, a plurality of semiconductor sensors configured to analyze the received bio-fluid, at least one reference electrode for biasing a bio-fluid gate of at least one of the semiconductor sensors, and at least one micro-fluidic or nano-fluidic channel in fluid communication with the at least one inlet, the at least one outlet and the at least one reference electrode; the at least one micro-fluidic or nano-fluidic channel includes the plurality of semiconductor sensors.

16 Claims, 7 Drawing Sheets

Figure 1A:
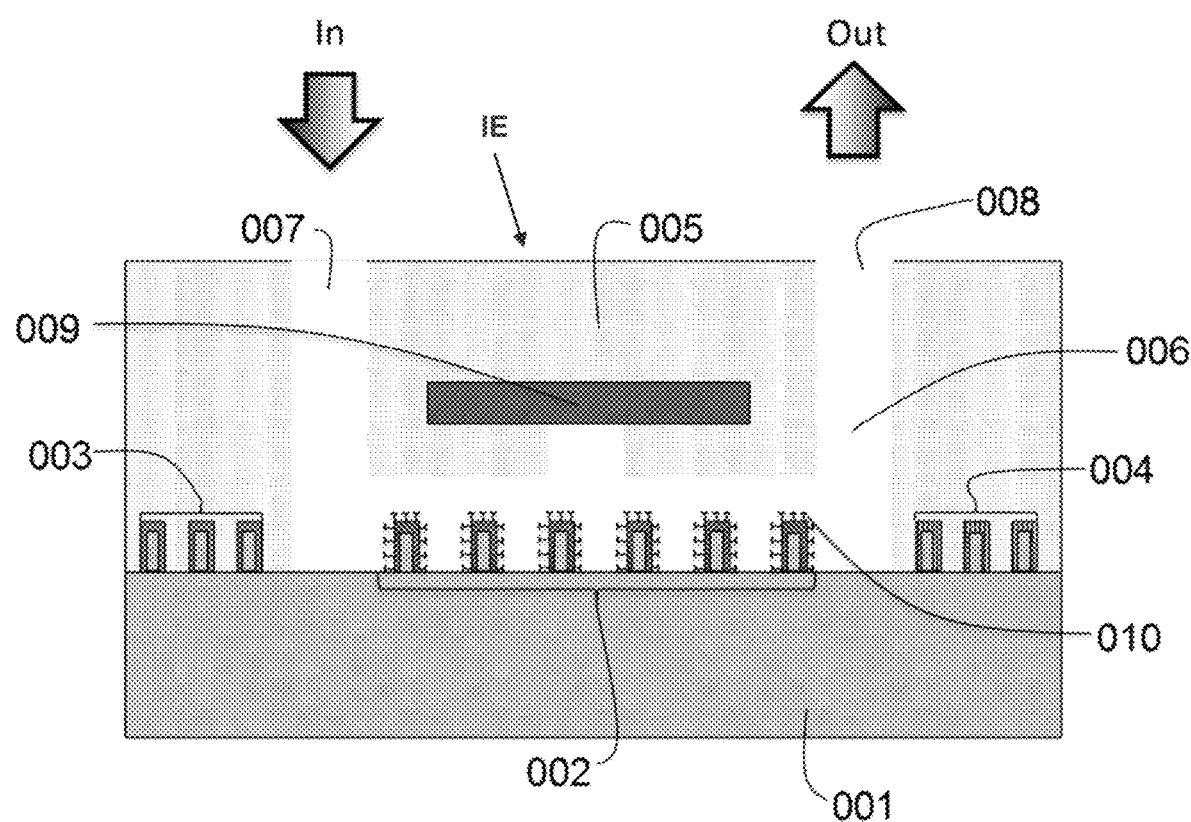

(51) Int. Cl.
  *A61B 5/1477* (2006.01)
  *A61B 5/15* (2006.01)
  *G01N 27/12* (2006.01)
  *G01N 33/543* (2006.01)
  *G01N 27/414* (2006.01)
  *A61B 5/157* (2006.01)

(52) U.S. Cl.
  CPC ....... *A61B 10/0045* (2013.01); *G01N 27/122* (2013.01); *G01N 33/54366* (2013.01); *A61B 5/157* (2013.01); *A61B 5/150022* (2013.01); *A61B 5/150969* (2013.01); *A61B 2562/028* (2013.01); *A61B 2562/0247* (2013.01); *A61B 2562/0271* (2013.01); *A61B 2562/0285* (2013.01); *A61B 2562/0295* (2013.01); *G01N 27/4145* (2013.01)

(58) Field of Classification Search
  CPC ...... A61B 2562/0271; A61B 5/150022; A61B 2562/0247; A61B 2562/028; A61B 2562/0285; A61B 2562/0295; A61B 5/150969; A61B 5/157; G01N 27/122; G01N 27/4145; G01N 33/54366–5438; G01N 27/327–3278; G01N 27/414–4148
  See application file for complete search history.

(56) References Cited

U.S. PATENT DOCUMENTS

| | | | | |
|---|---|---|---|---|
| 4,995,402 | A * | 2/1991 | Smith | A61B 5/157 206/569 |
| 5,174,299 | A * | 12/1992 | Nelson | A61B 5/028 600/505 |
| 6,616,823 | B2 * | 9/2003 | Kopf-Sill | B01L 3/502746 204/602 |
| 9,116,145 | B2 * | 8/2015 | Li | G01N 33/50 |
| 9,810,660 | B2 * | 11/2017 | Hu | G01N 27/4146 |
| 2001/0053535 | A1 * | 12/2001 | Bashir | G01N 33/56911 435/34 |
| 2004/0124147 | A1 * | 7/2004 | Fissell, IV | B01D 67/0088 210/650 |
| 2004/0129678 | A1 * | 7/2004 | Crowley | B01D 61/18 216/84 |
| 2005/0106713 | A1 * | 5/2005 | Phan | B01L 3/502738 435/287.2 |
| 2005/0241959 | A1 | 11/2005 | Ward et al. | |
| 2008/0154101 | A1 * | 6/2008 | Jain | A61B 5/14539 600/309 |
| 2009/0084678 | A1 * | 4/2009 | Joshi | G01N 27/4146 204/403.14 |
| 2009/0318790 | A1 * | 12/2009 | Fujiwara | A61B 5/14532 600/347 |
| 2010/0025238 | A1 * | 2/2010 | Gottlieb | A61B 5/14532 204/401 |
| 2010/0141280 | A1 * | 6/2010 | Yang | G01N 27/4145 324/692 |
| 2011/0034912 | A1 * | 2/2011 | de Graff | H01L 27/14687 606/21 |
| 2013/0056353 | A1 * | 3/2013 | Nemirovsky | G01N 27/4146 204/416 |
| 2013/0209991 | A1 * | 8/2013 | Wang | H01L 21/02104 435/5 |
| 2013/0291627 | A1 | 11/2013 | Hu et al. | |
| 2014/0134748 | A1 * | 5/2014 | Liu | B01L 3/502707 436/150 |
| 2015/0202626 | A1 * | 7/2015 | Huang | A61B 5/150022 422/82.01 |
| 2015/0268189 | A1 | 9/2015 | Rigante et al. | |
| 2015/0372119 | A1 * | 12/2015 | Zhang | B82Y 10/00 438/268 |
| 2016/0047775 | A1 * | 2/2016 | Roop | G01N 27/4148 204/406 |
| 2016/0310049 | A1 * | 10/2016 | Rowe | A61B 5/1477 |
| 2017/0119289 | A1 * | 5/2017 | Yoshioka | A61B 5/14546 |
| 2017/0238854 | A1 * | 8/2017 | Henshaw | A61B 5/1455 |
| 2017/0265789 | A1 | 9/2017 | Naseri et al. | |
| 2018/0064377 | A1 * | 3/2018 | Rogers | A61B 5/0059 |

OTHER PUBLICATIONS

European Search Report dated Feb. 8, 2017.
Craighead, Harold. "Future lab-on-a-chip technologies for interrogating individual molecules." Nature 442.7101 (2006): 387-393.
Gao, Wei, et al. "Fully integrated wearable sensor arrays for multiplexed in situ perspiration analysis." Nature 529.7587 (2016): 509-514.
Garcia-Cordero, Erick, et al. "Heterogeneous integration of low power pH FinFET sensors with passive capillary microfluidics and miniaturized Ag/AgCl quasi-Reference Electrode." Solid-State Device Research Conference (ESSDERC), 2016 46th European. IEEE, 2016.
Heikenfeld, Jason. "Non-invasive Analyte Access and Sensing through Eccrine Sweat: Challenges and Outlook circa 2016." Electroanalysis 28.6 (2016): 1242-1249.
Kim, Dae-Hyeong, Hyunjae Lee, and Tae Kyu Choi. "Graphene-based wearable electronic patch for diabetes control." Jun. 2016, SPIE Newsroom.
Zimmermann, Martin, et al. "Capillary pumps for autonomous capillary systems." Lab on a Chip 7.1 (2007): 119-125.
Livi, Paolo, et al. "A Hybrid FinFET-based Biosensor with Integrated Readout Capability." Procedia Engineering 47 (2012): 821-824.
Rigante, Sara, et al. "Sensing with Advanced Computing Technology: Fin Field-Effect Transistors with High-κ Gate Stack on Bulk Silicon." ACS nano 9.5 (2015): 4872-4881.
Safavieh, Roozbeh, and David Juncker. "Capillarics: preprogrammed, self-powered microfluidic circuits built from capillary elements." Lab on a Chip 13.21 (2013): 4180-4189.
Trenz, Florian, Robert Weigel, and Dietmar Kissinger. "Evaluation of a reflection based dehydration sensing method for wristwatch integration." Microwave, Radar and Wireless Communications (MIKON), 2016 21st International Conference on. IEEE, 2016.
Bluetooth from Silicon Labs, model: BLE112—https://www.silabs.com/products/wireless/bluetooth/bluetooth-low-energy-modules/ble112-bluetooth-sma.
Interfase Tag from AMS, model: AS3955 NFC—http://ams.com/eng/Products/Wireless-Connectivity/Sensor-Tags-Interfaces/AS3955.
International Search Report dated Nov. 15, 2017 for Application No. PCT/IB2017/055456.
International Written Opinion dated Nov. 15, 2017 for Application No. PCT/IB2017/055456.
Morak, J., Kumpusch, H., Hayn, D., Modre-Osprian, R., & Schreier, G. (2011). Design and evaluation of a telemonitoring concept based on NFC-enabled mobile phones and sensor devices. IEEE transactions on information technology in biomedicine, 16(1), 17-23.
Opperman, C. A., & Hancke, G. P. (Feb. 2011). A generic NFC-enabled measurement system for remote monitoring and control of client-side equipment. In 2011 Third International Workshop on Near Field Communication (pp. 44-49). IEEE.
Yi, W. J., Jia, W., & Saniie, J. (Aug. 2012). Mobile sensor data collector using Android smartphone. In 2012 IEEE 55th International Midwest Symposium on Circuits and Systems (MWSCAS) (pp. 956-959). IEEE.
European Office Action 94.3 dated Jan. 28, 2022 for Application N° 17783995.8.

* cited by examiner

Top Wafer [1]

a1 b1 c1 d1 e1 f1

Bottom wafer a2 b2 c2

Integration of Top and Bottom wafers l m n

BIO-FLUID COLLECTION AND SENSING DEVICE, SYSTEM AND METHOD

CROSS-REFERENCE TO RELATED APPLICATIONS

The present application claims priority to the European patent application with the application No. 16188227.9 that was filed on Sep. 10, 2016, the entire contents thereof being herewith incorporated by reference.

FIELD OF THE INVENTION

The present invention relates to a system, apparatus and method for collecting and sensing biological fluids on, for example, a human and also relates to a method for producing such an apparatus or system. The field of applications includes but is not limited to smart watches, smart patches, wrist-based devices and, at large, wearable devices for well-being, sport and healthcare applications. The system can provide the two mentioned functions when embedded in any object to which the skin or body of a human or animal is in contact. The device or system can be effortlessly and seamlessly transported by and worn on a human body for long periods of time (for example, hours or days) and allows on-body non-invasive and continuous bio-fluid monitoring over such long time periods.

BACKGROUND

Despite recent progress on wearable technologies, they are capable to offer only a glimpse of the physical state of a person with limited information, essentially focused on activity, sleep tracking and heart rate monitoring. However, the wellbeing and health status of humans are reflected by more combinations of parameters that are not currently monitored. For instance, access and continuous monitoring of different analytes in bio-fluids of an individual would enable to get a more complete and accurate picture of the health and wellness.

The biomarker monitoring technology according to the present disclosure can serve not only pure monitoring of the status but also enable, following specific data analytics, a large spectra of feedback services oriented towards an improved quality of life and prevention of life-style related diseases.

As of today, analyzing the biochemical composition of a biological fluid typically means an inconvenient blood test in laboratory: a process that is precise, but invasive and limited to well defined sampling moment in time. This type of process is non-continuous and invasive, drastically limiting its use or applications via existing lab-on-chip [see Ref 1] technologies for wearable applications. The consequence is that no wearable system or device today includes such an approach.

In parallel, various strategies aiming to reduce medical expenditure have directed the healthcare ecosystem to look into preventive health and consider alternatives to blood testing. One possibility, as set out in the present disclosure, is wearable, non-invasive and continuous bio-fluid monitoring such as sweat, saliva, tears, etc. Indeed, it has been shown [see Ref 2] that many of the biomarkers available in blood are also available in other bio-fluids, and particular diseases (cystic fibrosis, dehydration, diabetes etc.) have been associated with changes in biomarkers available in sweat for instance [and their detection [see Refs 3, 4].

Monitoring bio-fluids continuously, on-body and in real-time can also enable new studies on how an organism is regulating itself while exposed to different stimuli. Such requirements are driving new efforts into miniature, low power and highly compact sensor technologies, as the one proposed based on FinFETs [see Ref 5], which makes use of advanced computing technology adapted to answer all the needed specifications of wearable systems and is much in advance as size and low power consumption. The prior art falls short in terms novel and innovative technical elements to provide an on-body bio-fluid monitoring with continuous and real time capabilities and that can be effortlessly and seamlessly transported by and worn on a human body for long periods of time.

The device and system according to the present disclosure devises an approach for sensing or analyzing bio-fluids in real-time and in a non-invasive way, and is bodily wearable and suitable to wearable applications. The device or system according to the present disclosure can be effortlessly and seamlessly transported by and worn on a human body for long periods of time and allows on-body, non-invasive, and continuous bio-fluid monitoring over such long time periods. Some other systems proposed to date [see Ref 6], interesting as partial system functionality, are bulky and non-scalable to the needs of wearables.

A class of such applications are categorized as Lab-on-Skin™, an approach enabled by the system and method according to the present disclosure particularly focusing for example on biomarkers sensing in sweat based on on-chip system solutions. The system can be used for biomarker identification in any type of bio-fluid and, it can also be particularly used in or as a compact lab-on-chip.

SUMMARY

The present invention addresses the above mentioned inconveniences and problems of known systems and provides a fully integrated multi-function device or system on a single chip, capable of being used in any type of wearable application where a contact with the human skin or body occurs.

It is therefore one aspect of the present disclosure to provide an on-body wearable bio-fluid collection and sensing device that overcomes the above challenges. The on-body wearable bio-fluid collection and sensing device preferably includes an interface comprising at least one biocompatible material for contacting a bodily part, at least one inlet for receiving the bio-fluid, at least one outlet for evacuating the bio-fluid, a plurality of semiconductor sensors configured to analyze the received bio-fluid, at least one reference electrode for biasing a bio-fluid gate of at least one of the semiconductor sensors (002), and at least one micro-fluidic or nano-fluidic channel in fluid communication with the at least one inlet, the at least one outlet and the at least one reference electrode; the at least one micro-fluidic or nano-fluidic channel includes the plurality of semiconductor sensors.

According to another aspect of the present disclosure, the at least one reference electrode is fully embedded inside the device.

According to a further aspect of the present disclosure, the at least one micro-fluidic or nano-fluidic channel is configured to transfer the bio-fluid from the at least one inlet through the channel and out of the at least one outlet via capillary motion.

According to a yet another aspect of the present disclosure, the device is a bio-fluid collection and sensing lab-on-a-chip wearable device for on-body bio-fluid sensing.

According to another aspect of the present disclosure, the plurality of semiconductor sensors comprise semiconductor sensors configured to detect a plurality of different biochemicals or biomarkers in the received bio-fluid.

According to a further aspect of the present disclosure, the plurality of semiconductor sensors are included on a first semiconductor or through-silicon-via substrate and the at least one micro-fluidic or nano-fluidic channel is included on a second substrate, and the first and second substrates are connected one to the other and form an integral device.

According to yet another aspect of the present disclosure, the second substrate includes the least one reference electrode embedded therein to contact the bio-fluid.

According to a further aspect of the present disclosure, the device further includes a flow rate sensor configured to measure a flow rate of the bio-fluid through the at least one micro-fluidic or nano-fluidic channel; and/or a temperature sensor configured to measure a temperature of an object to which the device is in physical contact and/or the temperature of the bio-fluid; and/or a pressure sensor configured to measure a pressure value exerted by the bio-fluid in the at least one micro-fluidic or nano-fluidic channel.

According to yet another aspect of the present disclosure, the device further includes an electronic circuit interconnected to the plurality of semiconductor sensors, the circuit being configured to operate the plurality of semiconductor sensors and to collect measured data from the plurality of semiconductor sensors; and/or wherein the circuit is configured to operate the flow rate sensor, the temperature sensor and/or the pressure sensor and to collect measured data from the flow rate sensor, the temperature sensor and/or the pressure sensor.

According to yet another aspect of the present disclosure, the circuit is configured to detect in real-time and continuously a biochemical or biomarker by the determination of a change in the electrical conductivity of at least one semiconductor sensor.

According to yet another aspect of the present disclosure, the circuit is configured to simultaneous detect in real-time and continuously a plurality of different biochemicals or biomarkers by the determination of a change in the electrical conductivity of a plurality of semiconductor sensors.

According to yet another aspect of the present disclosure, the plurality of semiconductor sensors are CMOS-compatible.

According to yet another aspect of the present disclosure, the at least one micro-fluidic or nano-fluidic channel defines an internal volume of $\leq 1$ nL and $\geq 0.1$ nL; and/or wherein the device defines an external surface area $\leq 1$ $cm^2$ or $\leq 1$ $mm^2$.

According to yet another aspect of the present disclosure, the device is pump-less.

According to yet another aspect of the present disclosure, the plurality of semiconductor sensors extend in a first plane, and the at least one reference electrode extends in a second plane above said first plane.

Another aspect of the present disclosure concerns a wearable device or system including the on-body wearable bio-fluid collection and sensing device.

According to yet another aspect of the present disclosure, the wearable device is a skin patch device.

According to yet another aspect of the present disclosure, the wearable device includes a calculator configured to process data provided by the bio-fluid collection and sensing device.

According to yet another aspect of the present disclosure, the wearable device further includes a wireless communication means configured to transmit data measured or calculated by the wearable device or the bio-fluid collection and sensing device to an external device.

According to yet another aspect of the present disclosure, the wearable device further includes a calculator configured to carry out management of the energy usage of the wearable device.

The bio-fluid collection and biomarker sensing functions are co-integrated on-chip, operating like a compact and non-invasive lab-on-skin, which makes this system applicable to wearable applications.

Other functional components such as other type of sensors, local electronic processing of the signal, components for wireless communication of the sensed data, energy management component and an energy source, if needed, can be combined with the on-chip system to extend the functionality of the lab-on-skin according to the application scenario.

The above and other objects, features and advantages of the present invention and the manner of realizing them will become more apparent, and the invention itself will best be understood from a study of the following description with reference to the attached drawings showing some preferred embodiments of the invention.

A BRIEF DESCRIPTION OF THE SEVERAL VIEWS OF THE DRAWINGS

Figure 1B:
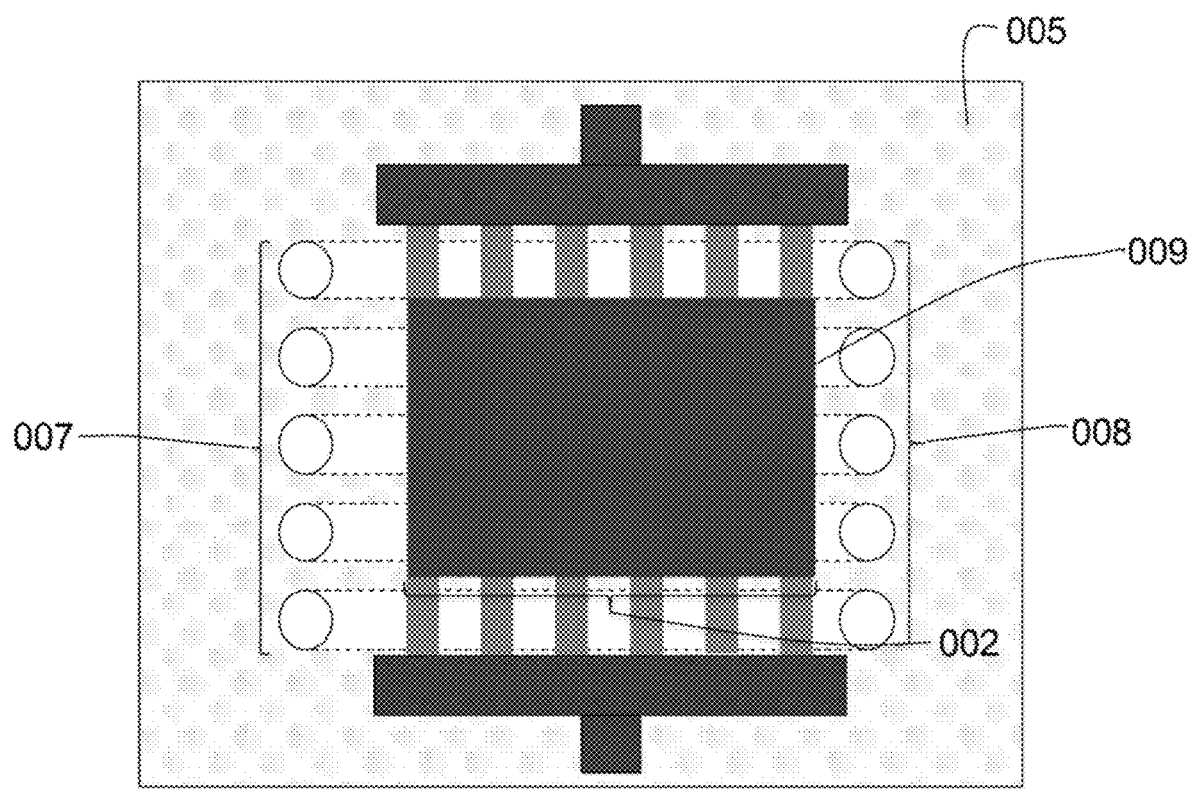
Figure 2:
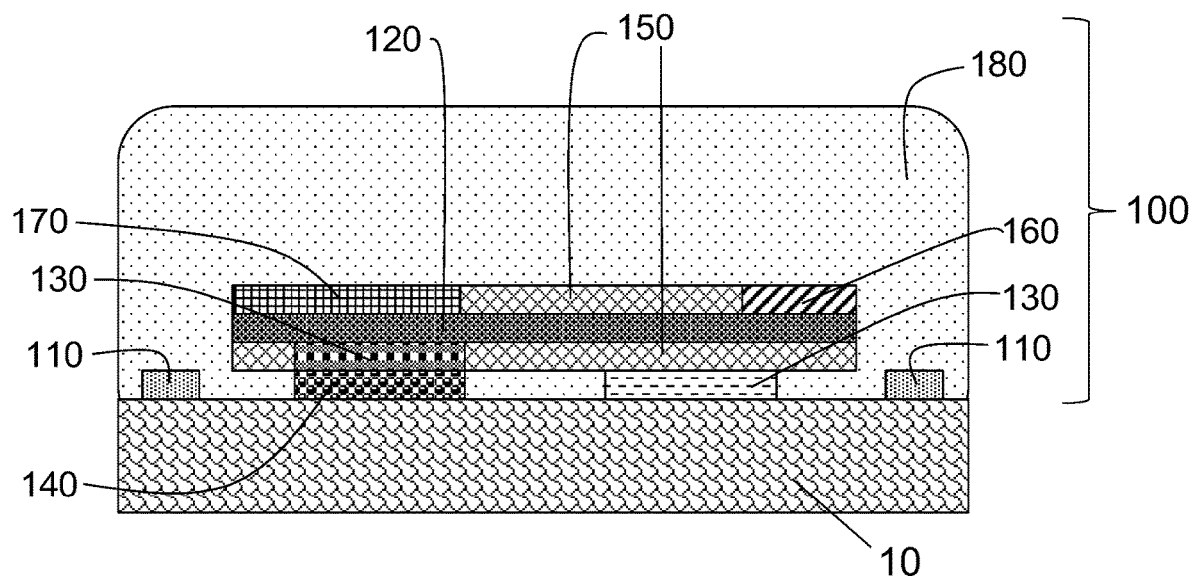
Figure 3A:
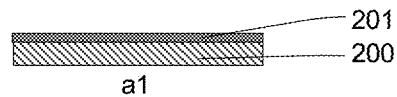
Figure 3A:
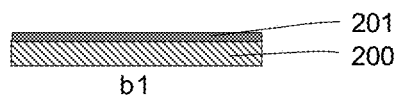
Figure 3A:
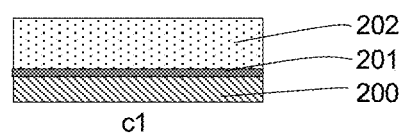
Figure 3A:
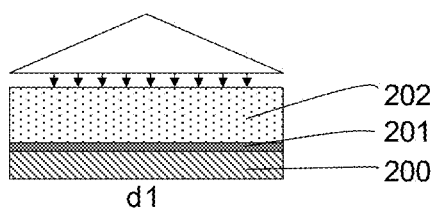
Figure 3A:
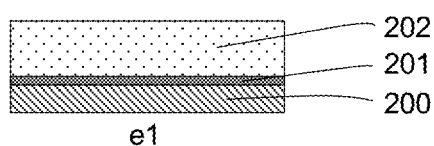
Figure 3A:
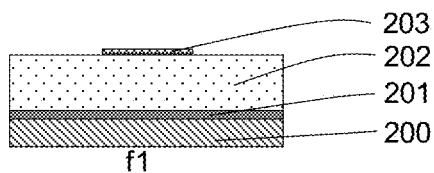
Figure 3B:
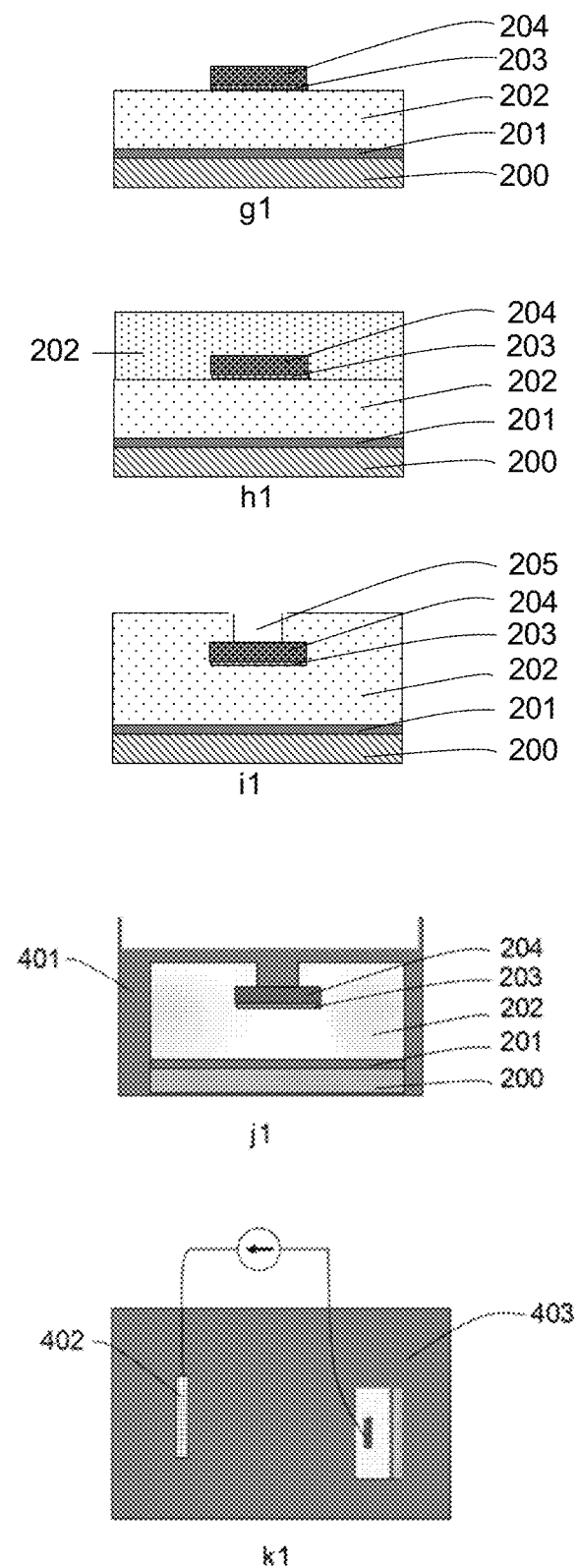
Figure 3C:
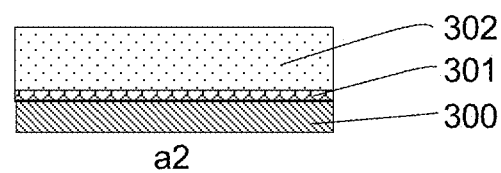
Figure 3C:
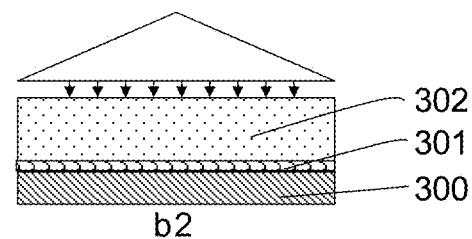
Figure 3C:
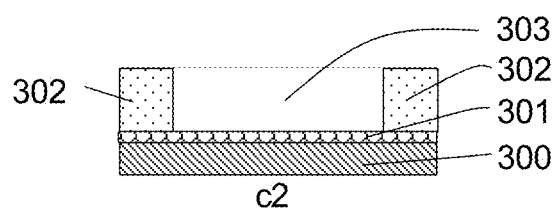
Figure 3D:
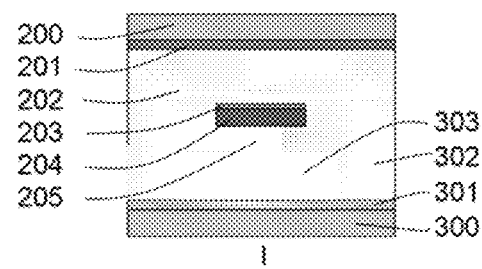
Figure 3D:
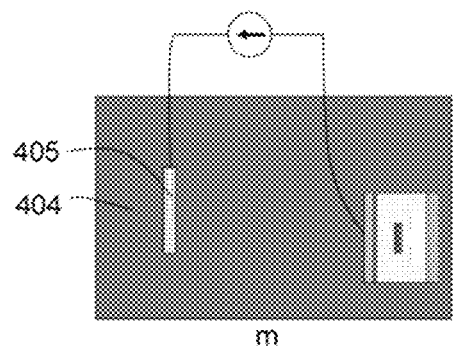
Figure 3D:
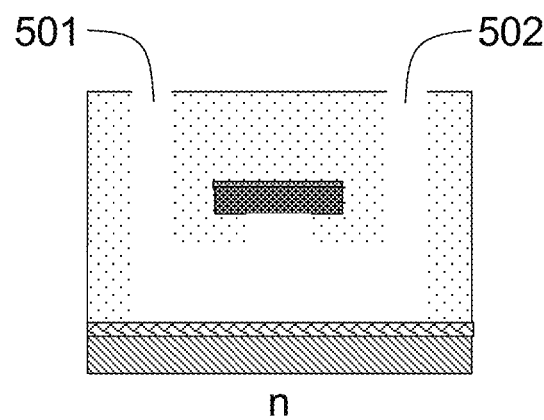

FIG. 1A is a cross-sectional schematic illustration of one embodiment of a device according to the present disclosure, the present disclosure combining into a compact system the sensor layer, the micro/nano-fluidics layer and the reference electrode, all integrated on-chip, this system can be placed in any type of object with which the skin or body of a human or animal is in contact; FIG. 1A depicts in cross-sectional view the various components of the integrated and compact system and method for collecting and sensing biofluids on a subject according to the disclosure where the 'In' and 'Out' arrows indicates the flow of the collected biofluid;

FIG. 1B is a top view of the system or device illustrated in FIG. 1A;

FIG. 2 depicts one particular patch embodiment of the proposed system or device according to the present disclosure, including extending the on-chip functionalities with other sensors and components, these other sensors and components and their functions are described in details in the following; the patch-like embodiment of the system or device of present disclosure includes heterogeneously integrated components and provides a small form factor system for the method for collecting and sensing bio-fluids on a subject's body; and FIGS. 3A to 3D show an exemplary full fabrication process flow, to demonstrate one possible method to achieve the on-chip integration of all the components and functions of the proposed system; FIGS. 3A and 3B show a process flow for the fabrication of an exemplary system or device according to the present disclosure including process steps for: the Top wafer—steps a1) to k1) (the chlorination for the integrated reference electrode is performed in steps j1 and k1 of the top wafer process); FIG. 3C shows the fabrication of the Bottom wafer—steps a2) to c2) and the integration of the Top and Bottom wafers is shown in steps 1) to n) of FIG. 3D.

DETAILED DESCRIPTION OF THE SEVERAL EMBODIMENTS

Various different embodiments of the present invention and different aspects of functionalities of the present invention are described below. It should be understood that they are presented to exemplify certain forms of the invention which are not intended to limit the scope of the invention.

FIGS. 1A and 1B illustrate an exemplary bio-fluid collection and sensing device according to the present disclosure.

The device comprises a plurality of inlets 007 for receiving the bio-fluid, a plurality of outlets 008 for evacuating the bio-fluid, an interface or interface surface IE comprising at least one biocompatible material for contacting a bodily part, a plurality of semiconductor sensors 002 configured to analyze the received bio-fluid, a reference electrode 009 (or a plurality of reference electrodes) for biasing a bio-fluid gate of the semiconductor sensors 002, and a plurality of micro-fluidic or nano-fluidic channels 006 in fluid communication with the inlets 007, the outlets 008 and the reference electrode 009. The micro-fluidic or nano-fluidic channels 006 include the plurality of semiconductor sensors 002.

The reference electrode 009 is fully embedded inside the device.

As illustrated in FIGS. 1A and 1B, the plurality of semiconductor sensors 002 can extend in a first plane, for example, substantially parallel to the first substrate 001 and/or the second substrate 005 and the reference electrode 009 extends in a second plane for example substantially parallel to the first substrate 001 and/or the second substrate 005 and located above the plurality of semiconductor sensors 002 and above the first plane in which the semiconductor sensors 002 extend. The reference electrode 009 can be, for example, a single reference electrode 009. The reference electrode 009 can, for example, extend in the second plane across multiple or all semiconductor sensors 002 as can be seen in FIG. 1B.

The micro-fluidic or nano-fluidic channels 006 are configured to transfer the bio-fluid from the inlets 007 through the channels 006 and out of the outlets 008 via capillary motion. The device is preferably a pump-less device.

The device is for example a bio-fluid collection and sensing lab-on-a-chip wearable device for on-body bio-fluid sensing. For example, a wearable device able to analyze the composition of a biofluid by electrically measuring a calibrated concentration of multiple biomarkers in the biofluid through the biochemical-electrical primary transduction of an array of sensors, each functionalized by immobilization of a specific probe material to detect a specific biomarker.

The plurality of semiconductor sensors 002 comprise semiconductor sensors 002 configured to detect a plurality of different biochemicals or biomarkers in the received bio-fluid.

In accordance with one embodiment, the device comprises a micro-fluidic or nano-fluidic layer to collect, handle biological fluids. In one embodiment, the fluidic layer includes passive microfluidics that may comprise one or a plurality of inlets, one or a plurality of channels, one or a plurality of outlets. The passive microfluidics are configured to collect and transfer a fluid from the inlet(s), through the channels and expel it at the outlet(s). At the base of and integrated with this microfluidic layer, the channels are in contact with a plurality of sensors 002 and one or more reference electrodes 009 (to provide a stable potential biasing the biofluid) that are wetted by the collected bio-fluid, enabling the sensing functions on the collected liquid.

The plurality of semiconductor sensors 002 are included on a first semiconductor or through-silicon-via substrate 001 and the micro-fluidic or nano-fluidic channels 006 are included on a second substrate 005. The first 001 and second 005 substrates are connected one to the other and form an integral device. The second substrate 005 comprises or consists of at least one biocompatible material such as, for example, SU-8 photo-epoxy.

The second substrate 005 includes the reference electrode 009 embedded therein to contact the bio-fluid. The second substrate 005 includes an opening and a micro-fluidic or nano-fluidic channel allowing the reference electrode 009 to be in fluidic communication with the bio-fluid.

The device can also include a flow rate sensor configured to measure a flow rate of the bio-fluid through the at least one micro-fluidic or nano-fluidic channel 006; and/or a temperature sensor 004 configured to measure a temperature of an object to which the device is in physical contact and/or the temperature of the bio-fluid; and/or a pressure sensor configured to measure a pressure value exerted by the bio-fluid in the at least one micro-fluidic or nano-fluidic channel 006.

The device can also include an electronic circuit 003 interconnected to the plurality of semiconductor sensors 002. The circuit 003 is configured to operate the plurality of semiconductor sensors 002 and to collect measured data from the plurality of semiconductor sensors 002.

The circuit 003 can also be configured to operate the flow rate sensor, the temperature sensor and/or the pressure sensor and to collect measured data from the flow rate sensor, the temperature sensor and/or the pressure sensor.

The circuit 003 is for example configured to detect in real-time and continuously a biochemical or biomarker by the determination of a change in the electrical conductivity of at least one semiconductor sensor 002.

The circuit 003 can be configured to simultaneous detect in real-time and continuously a plurality of different biochemicals or biomarkers by the determination of a change in the electrical conductivity of a plurality of semiconductor sensors 002.

The plurality of semiconductor sensors 002 can preferably be CMOS-compatible.

The plurality of sensors 002 may comprise temperature, pressure, flow rate, impedance sensors or biochemical sensors. Each biochemical sensor is functionalized by immobilization of a specific probe material on its sensitive transduction surface to selectively detect a specific targeted analyte/biomarker via specific interaction with the functionalization probe material. Each sensor therefore provides a response to a defined/targeted biochemical analyte (As an example, immobilization of glucose oxidase enzyme is commonly used as a functionalization of sensors for the selective sensing of glucose.)

Temperature, pressure, flow rate and concentrations of specific biochemical analytes within the biofluid can be electrically measured via the electrical signals of the plurality of sensors as primary transducers. The electrical signal parameters are a function of the temperature, pressure, flow rate or concentration of an analyte depending on the sensor type.

The sensors 004 are connected to the electronics module 003 that may notably include the read-out circuitry of the sensors to read their electrical signals and computing and logic circuitry (including processors, microcontroller) to, among other functions, associate the electrical signal parameters to numeric values of temperature, pressure, flow rate or concentration of an analyte based on the calibration of the sensors (sensitivity, offset, etc.).

Through the measurements, by means of the sensors, of the concentrations of multiple biochemical analytes within the biofluid, the device provides notably a biochemical analysis with the quantified composition of the biofluid.

The electronics module 003 may perform other signal and data processing. The electronics module can convert the analog signals of the sensors to digital ones (that can be processed by computers), it can perform analog and/or digital signal processing such as but not limited to filtering, noise reduction, Fast Fourier transform, etc. Through calculations or algorithms, the electronics can process or extract further data from the primary data of the sensors. For instance, the ionic strength of the biofluid can be calculated from the concentrations of the ions present in the biofluid, or the biochemical sensor response can be calibrated in temperature based on the temperature sensor response. The electronics module may include memories (such as Flash memories) to store the data.

The micro-fluidic or nano-fluidic channel or channels 006 define an internal volume of ≤1 nL and ≥0.1 nL.

The device defines an external surface area≤1 $cm^2$ or ≤1 $mm^2$. The external surface area is defined, for example, as the area defined by the outside perimeter shown in FIG. 1B.

The bio-fluid collection and sensing device can be included in a wearable device. The wearable device can be for example a skin patch device as illustrated in FIG. 2. The wearable device may include a calculator configured to process data provided by the bio-fluid collection and sensing device.

The wearable device may also include a wireless communication means configured to transmit data measured or calculated by the wearable device or the bio-fluid collection and sensing device to an external device.

The wearable device may further include a calculator configured to carry out management of the energy usage of the wearable device.

In accordance with an embodiment of the present disclosure, illustrated in FIGS. 1A and 1B, an integrated and compact system and method for collecting and sensing biofluids on a subject, and characterizing the biofluids' biochemical composition and measuring flow rates, temperatures and pressures, is provided.

The embodiment described corresponds to an on-chip integration of silicon sensors, micro/nano-fluidics and reference electrode. The silicon sensor layer can include arrays of sensors corresponding to multiple types of biomarkers. It can also include the read-out electronic circuits for the sensors and the analog-to-digital convertor circuits. The silicon sensor layer can be realized on traditional silicon wafer substrate but also on silicon-on-insulator (SOI), including ultra-thin body SOI, or other type of semiconducting substrates. It can be also realized on a TSV (through-silicon-via) substrate, which can facilitate embodiments based on thinned substrates for flexible substrate applications.

The system collects, via the micro/nano-fluidic layer, and senses, via the sensor layer, on-body bio-fluids that can be either excreted by the body (e.g. sweat or urine), secreted (e.g. tears or saliva), obtained with one or multiple needles (e.g. blood or interstitial fluids), or collected by other means (including invasive sampling) and deposited on the surface of the named system.

The system and method of the present disclosure may provide a non-invasive, continuous, real-time and wearable (biochemical) apparatus and technique for monitoring personal health data of a subject. As such, by the combination of these two functions and operation in real-time and non-invasively, the system is applicable to a lab-on-skin use for wearables, as per the following description, but it is not limited to.

The system of the present disclosure can achieve such small weight and small size (below 1 $cm^2$) that it can be readily worn on the body of an adult, infant and elderly as a frictionless device.

It can be also embedded into objects such as but not limited to wristbands, watches, band-aids, glasses, clothes, contact lenses, medical tools, implantable devices, wheel-drive of cars, and consumer electronics products. Its compactness, complemented by a real time operation for collection and analyzing of the biofluids, in less than seconds enable also its operation in any type of object with which the human skin or body is in contact.

FIGS. 1A and 1B shows the system on-chip embodiment of:

- a layer of nano-sensors, made on a substrate such as a silicon, silicon-on-insulator or a semiconductor wafer. These nano-sensors can be embodied like thin-film of Fin Field Effect Transistors (FETs), which are standard advanced microprocessor technologies, that are made in arrays functionalized to various biomarkers, providing a multi-parameter sensing. The sensing layer is CMOS-compatible, which enables the embodiments of temperature sensors based on semiconductor junctions, read-out circuitry and of analog-to-digital circuitry in the same semiconducting layer.
- a layer of micro/nano-fluidics, integrated by silicon-chip compatible processes on the based layer of nanosensors. This layer is made out of channels designed and produced in a bio-compatible material that have micrometer dimensions and can bring by capillarity mechanisms the bio-fluids collected at the inlets in amounts that can be as small as one nanoliter. The capillarity forces ensure a passive operation (no source of external energy needed) of this micro/nano-fluidic layer. The micro/nano-fludic layer has inlets, to collect the biofluid, and outlets, to evacuate the bio-fluid, via the fluidic channels, designed to ensure a dynamic quasi-continuous operation of the bio-fluid. At the bottom of this layer, the channels are in contact with the sensors that are wetted by the bio-fluid, enabling the sensing functions on the collected liquid.
- A reference electrode, which is used to bias the liquid gate of the FET sensors and provide the needed electrical condition for a calibrated and repeatable condition of sensing measurements. This electrode is made out of a material and based on a process that are compatible with the processing on-chip, is embeddable in the microfluidic layer and is scalable according to the dimensions imposed by the base chip including the sensing layer.

The significance of the various layers depicted in the cross-sectional and top views of FIGS. 1A and 1B is the following:

001: semiconducting substrate (i.e. silicon wafer or any other type of semiconducting substrate). It can also be a TSV substrate, thinned downed to ensure flexibility.

002: FinFET sensors with liquid gate or any other type of FET sensors, including multi-gate transistors, processed on a semiconductor.

003: FET based integrated circuitry (read-out, amplifiers and/or ADCs) using the traditional CMOS technology.

The metal interconnects to the source, drain and gate of these devices are not figured here, for simplification.

004: Temperature sensors using CMOS integrated circuits.

005: microfluidic material in which the channels are realized (for instance, SU8 in our exemplary process flow of FIG. 3)

006: microfluidic channels to conduct the collected bio-fluid to the sensing layer

007: inlets to collect the bio-fluid

008: outlets to expel the bio-fluid

009: the integrated reference electrode (its material structure and integration are described in FIG. 3).

The device or system operation is as it follows. The system top surface IE having the open inlets 007 is placed in contact with a source of bio-fluid (as, for instance, the surface of the human skins that has a certain number of pores via which the sweat is excreted, but not limited to).

The size and the density (number per unit of area) of inlets is designed such as there is an adapted collection of the bio-fluid that is transported via the micro-fluidic channels 006 without the need of a pump, due to capillary forces and then expelled via the outlets 008. Typical dimensions of the inlet are the order of few micrometers to tens of micrometers in diameter (when designed circularly), These channels are designed so that they are wetting the base sensor layer 002 and the reference electrode 009 with the collected fluid, enabling an electrical measurements of the sensor response. The dimensions of the channel or channels are determined such that a (desired optimized) laminar fluid flow is produced therein taking into account the (required) size of the sensors 002.

Each sensor is deigned based on an electrical principle so that it can detect in real-time a bio marker in the sweat by a change of its electrical conductivity. For instance, the sensors can be functionalized ion-sensitive FinFETs using a high-k dielectric around a thin semiconducting body, having the surrounding bio-fluid acting as a liquid gate while the source and drain contact of the FinFET are biased in a certain regime.

The functionalization of the surface of the FinFET is understood here as a specific selectivity of the device surface to detect biomolecular interactions. There are different ways to achieve this, depending on what the detection goal is.

For instance, pH can be detected directly by using a few monolayers of a high-k dielectric in the FET gate stack while to achieve other biomarker detection it is require to bind distinct molecular monolayers to specific regions of the gate of the device.

The proposed system can use a large number of FinFETs (from tens to thousands), each being differently functionalized and having a specific electrical response to a given biomarker.

The detection can be achieved electrically by for example a change of conductivity that is detected as a change in a measured voltage or current, depending on the method used.

The FinFET can be biased in weak (low gate voltage) or strong inversion (large gate voltage), in linear (low drain voltage) or saturation (large drain voltage) regimes, providing a tunable gain of the device and a tunable sensitivity. Depending on the goals of an optimal detection (maximization of the sensitivity and/or power consumption) the regime of sensor operation can be simply adjusted by selecting the values of the drain and gate voltages. This choice is completely independent of the operation of the micro/nanofluidic layer.

The output of the sensor can be a current level (for instance, the drain current) or a voltage level (for instance, the drain voltage) that is changed by the presence of a different concentration of a given biomarker in the biofluid, which acts as a change in the potential applied to the gate of the FinFET.

This type of output is of analog nature (a continuously changing electrical signal). In the system or device according to the present disclosure, metal-gate FinFETs fabricated in the same technology as the FinFET sensors can be used to build analog readout circuitry and analog-to-digital converters so that the output of the signal on the same chip can be of digital nature. That is to say the same front-end-technology can be used to fabricate both metal-gate transistors, used as elementary building blocks of electronic circuits, and the sensor transistors; the sensor devices can have a customized architecture, by replacing and/or opening access to the gate channel (with and without metal gate).

The circuitry/electronics 0003 can for example be configured to carry out the above functions concerning the sensor (FinFET) operation and current or voltage level change detection as well as readout, A/D conversion, and analog and digital signal processing.

Alternatively, instead of the proposed FinFET sensors any other type of thin-body field-effect devices can be used.

These sensors are designed in arrays functionalized to various types of biomarkers, allowing the simultaneous detection of a many biomarkers during in the same collected biofluid.

The biochemical sensors can be functionalized with a plurality of functionalizations for selective detection of different target analytes including, for example, ions, molecules, proteins, enzymes, hormones, bacteria in order to enable multi-parametric sensing.

The outputs of these arrays are connected to the read out (CMOS) circuitry 003 that can be also have designed and implemented in the same technology and analog-to-digital conversion (this function can be also external, depending on the required sensor output: analog or digital).

In parallel with the biomarker measurement, the base sensor layer can execute a temperature measurement that can be used for sensor calibration but also as an object, environment or skin/body temperature measurements, depending on the object with which the top layer of the sensor is in contact.

FIG. 2 shows a patch embodiment according to another aspect of the present disclosure with heterogeneously integrated components and small form factor system (100) and the method for collecting and sensing biofluids on a subject's body (10) includes (and heterogeneously integrates part or all of the following elements): a fixature (or attachment) module (110), a substrate (120), a sensor module (130), a micro/nano-fluidic module (140), an electronics module (150) which may include a communication module (160) and an energy supply module (170), and an envelope (180).

The system includes the abovementioned fixature module (110) which provides means to place and keep in place the system on the subject's body (10). According to the embodiments, the fixature module (110) may have various properties including but not limited to adhesivity, hydrophilicity, hydrophobicity, permeability and impermeability to sweat solutes or solvent, electrical conductivity, insulation, thermal conductivity, insulation.

The system includes the abovementioned carrier substrate (120) on which may be placed the electronics module (150), the communication module (160), the energy supply module (170), the sensor module (130). Exemplary carrier substrates are FR-4 PCB substrates, Kapton film, etc. The substrate (120) may provide connections on and between its surfaces.

The system or device of FIG. 2 may include the device of FIGS. 1A and 1B as described previously and shown, for example, in FIG. 2 as sensor module 130 and fluidic module 140. However, the system or device of FIG. 2 does not necessarily include the device of FIGS. 1A and 1B and may thus include (instead of or in addition to the device of FIG. 1) one or more bio-fluid sensors employing different sensing technologies as shown for example by the sensor 130 in FIG. 2 directly in contact with an object 10.

The system includes the abovementioned sensor module (130) which comprises one or a plurality of sensors and one or a plurality of miniaturized reference electrodes (which can alternatively be included in the fluidic module 140).

Without claiming exhaustiveness, the module 130 may include flow rate sensors notably to measure sweat rate, pressure sensors notably to measure sweat pressure in the system, skin impedance sensors, temperature sensors notably to measure sweat temperature, local skin temperature at contact interface between the system and the skin, core-body temperature and environmental temperature notably the temperature of the air surrounding the system. Such temperature sensors may be used in particular for the calibration in temperature of other sensors.

The module 130 may also include sensors for sensing sweat regarding its (biochemical) composition notably biomarkers, solutes, solvent. A plurality of biochemical sensors can be functionalized (with a plurality of functionalizations) towards selective detection of different target analytes, including but not limited to ions, molecules, proteins, enzymes, hormones, bacteria, to enable multi-parametric sensing.

Sensors of the sensor module (130) may be of the same or different types of sensing technologies. For example, biochemical sensors for sensing the sweat composition may be but are not limited to electrochemical potentiometric, amperometric sensors, field effect transistor sensors, tunnel field effect transistors, bipolar transistor sensors, MEMS sensors.

The sensor module (130) may include abovementioned reference electrodes that are not sensors per se but are indispensable elements to the proper operation of certain biochemical sensing technologies. The reference electrodes may be notably made of noble metals, silver-silver chloride with or without coating of a polymer membrane. A significant feature of the reference electrodes is that they are miniaturized (classic commercial reference electrode have typically a pen size) and integrated/embedded within the sensor module (130) and fluidic module (140) ensemble (as explained below) and as such may be in contact with the collected fluid (e.g. sweat). The reference electrode of the device of FIGS. 1(a) and (b) may also include such characteristics.

The sensor module (130) may be connected to the electronics module (150) on the substrate (120) and to the fluidic module (140) as will be further explained below.

The system includes the abovementioned fluidic module (140) to collect, handle biological fluids on the body of a subject, for example sweat on the skin. In one embodiment, the fluidic module (140) are passive microfluidics that can be made of polymers, resins, oxides, glass, silicon, to name but a few, in a way adapted to contact human body. They may comprise one or a plurality of inlets, one or a plurality of channels, one or a plurality of outlets, one or a plurality of specific structures, notably to control the flow of a fluid or evacuate an excess of fluid. The micro-fluidic or nano-fluidic channels 006 of the device of FIGS. 1A and 1B may also include such characteristics.

Passive microfluidics do not require any external power supply to operate and are self-powered/autonomous. The passive microfluidics can exploit capillarity and surface tension effects to collect a fluid (e.g. direct collection of sweat freshly exuded from the sweat ducts on the skin) at the inlet(s), handle and circulate the fluid through channels and expel it at the outlet(s).

The passive microfluidics may include on a surface in contact with the subject's body (10) sealing elements, membranes or a localized surface treatments or patterning producing properties such as but not limited to hydrophobicity to selectively prevent contamination of the biofluid collected at the inlets from external sources: for instance rain or old, mixed, degraded biofluid flowing from other areas of the subject body; or from sources of the subject's body (10): for instance desquamation, solid biological objects and debris, sebum. Outlets of the passive microfluidics are disposed to expel the biofluid outside the inlet collection area, in particular to avoid contamination through mixing. The biofluid may be expelled at the outlet(s) outside the system or in an absorbent material. The micro-fluidic or nano-fluidic channels 006 of the device of FIGS. 1A and 1B may also include such characteristics.

The microfluidics may be designed so as to provide a unidirectional and/or laminar (non-turbulent) flow of the fluid, notably impeding any reflow or mixing with "old" biofluid or external contamination. The microfluidics may be designed with such dimensions so as to require a volume of biofluid below 1 nL to be filled and operate the system (in normal regime/in steady state). Such a feature advantageously enables notably the on-body, continuous and real-time operation and the collection of health data in all daily life scenarios of a subject including for instance low sweat rate conditions of a subject (such as rest in a mild climate). The micro-fluidic or nano-fluidic channels 006 of the device of FIGS. 1(a) and (b) may also include such characteristics.

The fluidic module (140) may be directly fabricated and integrated in a monolithic fashion on the sensor module (130) as a post-process. As such the sensor module (130) and the fluidic module (140) may be created in a single production flow and do not need to be separately produced and subsequently aligned, bonded, connected or assembled. Such a feature is of particular interest as sensors, in particular their sensitive transduction surface, and the miniaturized reference electrode may be embedded within the fluidics and may be in contact with the collected fluid providing a monolithic and miniaturized fluidic-sensing cell.

The system includes the abovementioned electronics module (150). It may be placed with the energy supply module (170) and the communication module (160) on the substrate (120) and connected to the sensor module (130). By way of example, the electronics module (150) may perform the following: sensor excitation and readout, analog to digital conversion, DC-DC boost conversion, signal acquisition and processing, data storage, power management, communication management. Exemplary components that the electronics module (150) may include without exhaustiveness are microcontrollers, memories, crystal oscillators.

The system includes the abovementioned energy supply module (170) which supplies the power necessary to operate the device or system and is connected to the electronics module (150). It may include components such as rigid batteries, flexible batteries, bendable and printed batteries, energy harvesters and other useful components.

The system includes the abovementioned communication that is interfaced with the electronics module (150), provides communication means between the system and other communication-enabled devices and notably enables to transmit the health data measured by the system to a smart hub (typically smartphone) and display it to the end user. In one embodiment of the present disclosure, the communication module (160) provides wireless communication capabilities and may include components such as Bluetooth circuit, near field communication transponder, antennas that may be printed on the substrate (120).

The system includes the abovementioned body or envelope (180) that envelops, covers the other parts of the system. Exemplary materials of the envelope may be polymers such as polyethylene, polyurethane or polyvinyl chloride.

According to the embodiments, the envelope (180) may have various properties in particular selective permeability or impermeability to liquids or gases. For instance, an envelope (180) impermeable to gases and liquids provides an enclosure of the contact area between the system and the subject's body, that may be further supplemented by the fixature module (110), and offers a protection against external contamination of the system and if the biofluid collected by the system.

In a method and system in accordance with one embodiment of the present disclosure, the device or system is placed, for example, on the body of subject with the passive microfluidic module surface in contact with the body.

Biofluid excreted or secreted from the subject's body (10) is continuously collected at the inlet(s), flows through and fills (almost instantaneously <1 s) the channels of the passive microfluidics and is expelled at the outlets.

The biofluid wets both a plurality of sensors transduction surfaces and miniaturized reference electrodes integrated within the microfluidics. The plurality of sensors, according to their functions, provide electrical signals corresponding to the temperature, pressure, flow rate or concentrations of specific biochemical analytes (e.g. relevant biomarkers to monitor the health status of a subject) respectively. The sensors are connected to the electronics module (150) and wireless communication module (160) which in turn condition and transmit wirelessly the signals to a data acquisition module of a nearby mobile device, with methods such as Bluetooth or near-field communication.

The energy necessary to operate the sensor module (130), electronics module (150) and wireless communication module (160) are either supplied by the energy supply module (170) or alternatively by a mobile device through a wireless power transfer scheme. The mobile device is equipped with an adequate processing unit to treat the signals, extract, interpret and display health data.

In a method and system in accordance with another embodiment of the present disclosure, a sample of biofluid is dropped or placed at the inlets of the of the passive microfluidic module. Biofluid flows through and fills the channels of the passive microfluidics wetting both a plurality of sensors transduction surfaces and miniaturized reference electrodes integrated within the microfluidics. The plurality of sensors, according to their functions, provide electrical signals corresponding to the temperature, pressure, flow rate or concentrations of specific biochemical analytes (e.g. relevant biomarkers to monitor the health status of a subject) respectively.

The sensors are connected to the electronics module (150) and wireless communication module (160) which in turn condition and transmit wirelessly the signals to a data acquisition module of a nearby mobile device, with methods such as Bluetooth or near-field communication. The energy necessary to operate the sensor module (130), electronics module (150) and wireless communication module (160) are whether supplied by the energy supply module (170) or alternatively by a mobile device through a wireless power transfer scheme.

The mobile device is equipped with an adequate processing unit to treat the signals, extract, interpret and display health data.

FIGS. 3A to 3D detail an exemplary process for producing silicon based sensors, reference electrode and passive microfluidics in a monolithic integration scheme, and as is follows:

Top Wafer Processing:
starting substrate is a low-doped p-type silicon substrate (200).
a1) 50 nm Aluminum sacrificial layer (201) is deposited on top of front side of the top wafer.
b1) wafers are cleaned with oxygen plasma for 7 minutes at 500 W before the SU-8 procedure.
c1) 5 µm layer of SU-8 (202) is spin-coated. Then, the photo resist is baked for 25 min at 130° C.
d1) wafers are exposed to UV light on a back-side mask aligner for 6 seconds at an intensity 10 mW/cm2.
e1) Wafer baking is executed at 90° C. for 90 minutes to achieve cross-linking.
f1) a short surface treatment (30 s at 200 W) of oxygen plasma is used on the SU-8 wafers prior to metal deposition. Metals are deposited on top of the SU-8 layer. The metals are deposited by sputtering. First, 46 nm of Chromium (203) is deposited as an adhesive layer.
g1) 900 nm of silver (204) is deposited with the same machine.
h1) a 5 µm layer of SU-8 (202) is spin coated and exposed to create a small reservoir (205).
i1) SU-8 is developed to obtain access to the reference electrode Chlorination Steps:
j1) samples are dipped in a diluted solution of HNO3 (401) for three minutes and rinsed with deionized water two times.
k1) the silver electrode sample is placed in the anode, and a platinum thin-film counter electrode (402) was placed on the cathode. Both electrodes were dipped in a diluted KCl solution (403). An electrical current is applied through the interface.

Bottom Wafer Processing:
Starting substrate is a low-doped p-type silicon substrate (300) on which are fabricated semiconductor sensors (301) such as FinFET sensors whose fabrication is further discussed in US2015/0268189, filed Mar. 19, 2014, which is incorporated herein by reference in its entirety.
a2) a layer of SU-8 resin (302) is developed to spin coated to a thickness of 50 µm.
b2) SU-8 is exposed for 6 seconds at an intensity 10 mW/cm2.
c2) SU-8 is developed to obtain the channels (303).

Integration of Top and Bottom Substrates:
l) a constant pressure is applied at a 125° C. for 60 minutes. The described process allows both wafers to bond since the used temperature allows crosslinking of the resin.
m) Aluminum sacrificial layer is dissolved by anodization. The wafer sandwich is submerged in a diluted NaCl solution (404) and voltage is applied to it. A Platinum layer (405) anode was used as a counter electrode.

N) inlets (501) and outlet (502) are opened by using an Excimer laser by applying 100 times a 100 Hz burst with a 2.3 mJ energy.

The above-mentioned steps in FIG. 3 describe a method to fabricate a double layer SU-8 autonomous capillary microfluidic device with an embedded Ag/AgCl quasi reference electrode on top of a Si-Wafer with FinFET sensors. The hydrophilicity of SU-8 enables to displace liquid from inlets to outlets only by capillary forces. A double layer process was proposed in order to fabricate the sensing devices on one wafer and the microfluidics and reference electrode in a second wafer. This solution prevents cross contamination of the sensing layer of our ISFETs with the anodization that creates the Silver Chloride layer of the reference electrode. Further details of the fabrication and integration of the reference electrode can be found in the article entitled "Ultra-Low Power Ion-Sensing Smart Platform for Noninvasive Healthcare Applications" by Garcia Cordero et al, Smart Systems Integration, Munich, Germany, Mar. 9-10, 2016, available in Proceedings Smart Systems Integration ISBN 978-3-95735-040-4.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

[Ref 1] H. Craighead, *Future lab-on-a-chip technologies for interrogating individual molecules*, Nature 442, 387-393 (27 Jul. 2006)|doi:10.1038/nature05061.

[Ref 2] J. Heikenfeld, *Non-invasive Analyte Access and Sensing through Eccrine Sweat: Challenges and Outlook circa 2016*, Volume 28, Issue 6, June 2016, pp. 1242-1249.

[Ref 3] F-Trenz, R. Weigel, D. Kissinger, *Evaluation of a Reflection Based Dehydration Sensing Method for Wristwatch Integration,* 2016 21st International Conference on Microwave, Radar and Wireless Communications (MIKON), June 2016.

[Ref 4] D.-H. Kim, H. Lee and T. K. Choi, *Graphene-based wearable electronic patch for diabetes control*, June 2016, SPIE Newsroom. DOI: 10.1117/2.1201605.006498.

[Ref 5] S. Rigante, P. Scarbol, M. Wipf, R. L. Stoop, K. Bedner, E. Buitrag, A. Bazigos, D. Bouve, M. Calame, C. Schönenberger, and A. M. Ionescu, Sensing with Advanced Computing Technology: Fin Field-Effect Transistors with High-k Gate Stack on Bulk Silicon, ACS Nano, 2015, 9 (5), pp 4872-4881, DOI: 10.1021/nn5064216.

[Ref 6] W. Gao, S. Emaminejad, H. Y. Y. Nyein, S. Challa, K. Chen, A. Peck, H. M. Fahad, H. Ota, H. Shiraki, D. Kiriya, D.-H. Lien, G. A. Brooks, R. W. Davis. A. Javey, Fully integrated wearable sensor arrays for multiplexed in situ perspiration analysis, Nature 529, 509-514 (28 Jan. 2016) doi:10.1038/nature16521

The invention claimed is:

1. An on-body wearable skin patch for collection and sensing sweat from a wearer, the skin patch comprising:
    an interface having an interface surface comprising a biocompatible material for contacting a skin of the wearer;
    an inlet arranged in the interface surface for receiving the sweat excreted from the skin, the inlet configured to collect the sweat from the skin via capillary action;
    an outlet configured to expel the sweat by capillary action;
    a plurality of semiconductor sensors configured to analyze the sweat;
    a reference electrode for biasing a bio-fluid gate of at least one of the semiconductor sensors; and
    a micro-fluidic or nano-fluidic channel in fluid communication with the inlet, the outlet, and the reference electrode, the microfluidic or nano-fluidic channel including the plurality of semiconductor sensors,
    wherein the micro-fluidic or nano-fluidic channel extends between the inlet and the outlet and is configured to transfer the sweat from the inlet through the microfluidic or nano-fluidic channel via capillary action,
    wherein the plurality of semiconductor sensors are included on a first substrate and the micro-fluidic or nano-fluidic channel is included on a second substrate, and the first and second substrates are connected one to the other, and
    wherein the second substrate includes the reference electrode embedded therein to contact the sweat.

2. The on-body wearable skin patch according to claim 1, wherein the reference electrode is fully embedded inside the skin patch.

3. The on-body wearable skin patch according to claim 1, wherein the plurality of semiconductor sensors are configured to detect a plurality of different biochemicals or biomarkers in the sweat.

4. The on-body wearable skin patch according to claim 1, further including a flow rate sensor configured to measure a flow rate of the sweat through the micro-fluidic or nano-fluidic channel; and
    a temperature sensor configured to measure a temperature of the skin and a temperature of the sweat; and
    a pressure sensor configured to measure a pressure value exerted by the sweat in the micro-fluidic or nanofluidic channel.

5. The on-body wearable skin patch according to claim 4, further including an electronic circuit interconnected to the plurality of semiconductor sensors, the circuit being configured to operate the plurality of semiconductor sensors and to collect measured data from the plurality of semiconductor sensors, and
    wherein the circuit is configured to operate the flow rate sensor, the temperature sensor and the pressure sensor and to collect measured data from the flow rate sensor, the temperature sensor and the pressure sensor.

6. The on-body wearable skin patch according to claim 5, wherein the circuit is configured to detect in real-time and continuously a biochemical or biomarker by the determination of a change in the electrical conductivity of at least one semiconductor sensor.

7. The on-body wearable skin patch according to claim 5, wherein the circuit is configured to simultaneously detect in real-time and continuously a plurality of different biochemicals or biomarkers by the determination of a change in the electrical conductivity of the plurality of semiconductor sensors.

8. The on-body wearable skin patch according to claim 1, wherein the plurality of semiconductor sensors are CMOS-compatible.

9. The on-body wearable skin patch according to claim 1, wherein the micro-fluidic or nano-fluidic channel defines an internal volume of $\leq 1$ nL and $\geq 0.1$ nL.

10. The on-body wearable skin patch according to claim 1, wherein the skin patch is pump-less.

11. The on-body wearable skin patch according to claim 1, wherein the plurality of semiconductor sensors extend in a first plane, and the reference electrode extends in a second plane above the first plane.

12. The on-body wearable skin patch according to claim 1, further comprising:
a wireless communication device configured to transmit data measured or calculated by the on-body wearable skin patch to an external device.

13. The on-body wearable skin patch according to claim 1, further comprising:
a calculator configured to carry out management of the energy usage of the skin patch.

14. The on-body wearable skin patch according to claim 1, wherein the biocompatible material of the interface surface provides for hydrophilicity to the inlet for the capillary action.

15. The on-body wearable skin patch according to claim 1, wherein dimensions of the micro-fluidic or nano-fluidic channel are configured to generate a laminar fluid flow therein.

16. An on-body wearable bio-fluid collection and sensing device, the device comprising:
an interface comprising at least one biocompatible material for contacting a bodily part of a wearer;
at least one inlet for receiving the bio-fluid;
at least one outlet for evacuating the bio-fluid;
a plurality of semiconductor sensors configured to analyze the bio-fluid;
at least one reference electrode for biasing a bio-fluid gate of at least one of the semiconductor sensors; and
at least one micro-fluidic or nano-fluidic channel in fluid communication with the at least one inlet, the at least one outlet and the at least one reference electrode, the at least one micro-fluidic or nano-fluidic channel including the plurality of semiconductor sensors,
wherein the at least one inlet is formed in the interface,
wherein the at least one inlet is configured to directly contact the bodily part of the wearer and to collect the bio-fluid from the bodily part via capillary action,
wherein the at least one micro-fluidic or nano-fluidic channel extends between the at least one inlet and the at least one outlet and is configured to transfer the bio-fluid from the at least one inlet through the at least one micro-fluidic or nano-fluidic channel via capillary action,
wherein the bio-fluid is expelled from the at least one outlet via capillary action,
wherein the plurality of semiconductor sensors are included on a first semiconductor or through-silicon via substrate and the at least one micro-fluidic or nano-fluidic channel is included on a second substrate, and the first and second substrates are connected one to the other and form an integral device, and
wherein the second substrate includes the at least one reference electrode embedded therein to contact the bio-fluid.

* * * * *